(12) United States Patent
Burrows

(10) Patent No.: US 9,991,681 B2
(45) Date of Patent: Jun. 5, 2018

(54) RELAY-MOD METHOD TO DRIVE CORONA IGNITION SYSTEM

(71) Applicant: Federal-Mogul Ignition Company, Southfield, MI (US)

(72) Inventor: John Antony Burrows, Timperly (GB)

(73) Assignee: Federal-Mogul Ignition Company, Southfield, MI (US)

( * ) Notice: Subject to any disclaimer, the term of this patent is extended or adjusted under 35 U.S.C. 154(b) by 741 days.

(21) Appl. No.: 14/568,330

(22) Filed: Dec. 12, 2014

(65) Prior Publication Data

US 2015/0171601 A1    Jun. 18, 2015

Related U.S. Application Data

(60) Provisional application No. 61/915,088, filed on Dec. 12, 2013, provisional application No. 61/931,131, (Continued)

(51) Int. Cl.
*H01T 19/00*    (2006.01)
*H01T 15/00*    (2006.01)
(Continued)

(52) U.S. Cl.
CPC .............. *H01T 19/00* (2013.01); *F02P 23/04* (2013.01); *G01M 15/02* (2013.01); *G01N 27/02* (2013.01);
(Continued)

(58) Field of Classification Search
CPC .. F02P 9/00; F02P 23/04; H01T 15/00; H01T 19/00
See application file for complete search history.

(56) References Cited

U.S. PATENT DOCUMENTS 4,208,992 A    6/1980  Polo
5,149,940 A    9/1992  Davis et al.
(Continued)

FOREIGN PATENT DOCUMENTS

CN    101351638 A    1/2009
CN    101743395 A    6/2010
(Continued)

OTHER PUBLICATIONS

International Search Report, dated Mar. 25, 2015 (PCT/US2014/069952).

(Continued)

*Primary Examiner* — Thienvu Tran
*Assistant Examiner* — Christopher Clark
(74) *Attorney, Agent, or Firm* — Robert L. Stearns; Dickinson Wright, PLLC

(57) ABSTRACT

A corona ignition system for maintaining a drive frequency approximately equal to the resonant frequency of a corona igniter is provided. The system includes a current sensor, at least two cascaded timers which are electrically independent of a controller, and at least two switches. During operation, the current sensor measures the current at an input of the corona igniter. A conditioned current signal including information related to the zero crossings of the current ultimately activates a pair of the timers which in turn control and drive one of the switches. The conditioned current signal is not processed by the controller before driving the switch.

20 Claims, 4 Drawing Sheets

Related U.S. Application Data filed on Jan. 24, 2014, provisional application No. 61/950,991, filed on Mar. 11, 2014, provisional application No. 62/072,530, filed on Oct. 30, 2014, provisional application No. 62/090,096, filed on Dec. 10, 2014.

(51) Int. Cl.

| | | |
|---|---|---|
| *F02P 23/04* | (2006.01) | |
| *G01M 15/02* | (2006.01) | |
| *G01N 27/02* | (2006.01) | |
| *H02M 3/00* | (2006.01) | |
| *F02P 3/04* | (2006.01) | |
| *F02P 5/15* | (2006.01) | |
| *F02P 17/00* | (2006.01) | |

(52) U.S. Cl.
CPC .............. *H01T 15/00* (2013.01); *H02M 3/00* (2013.01); *F02N 2300/2011* (2013.01); *F02P 3/0407* (2013.01); *F02P 5/1502* (2013.01); *F02P 17/00* (2013.01)

(56) References Cited

U.S. PATENT DOCUMENTS

| | | | |
|---|---|---|---|
| 5,179,928 A | 1/1993 | Cour et al. | |
| 5,361,737 A | 11/1994 | Smith et al. | |
| 5,513,618 A | 5/1996 | Rich et al. | |
| 5,568,801 A | 10/1996 | Paterson et al. | |
| 6,758,199 B2 | 7/2004 | Masters et al. | |
| 6,883,507 B2 | 4/2005 | Freen | |
| 7,956,543 B2 | 6/2011 | Agneray et al. | |
| 7,974,068 B2 | 7/2011 | Agneray et al. | |
| 8,342,147 B2 | 1/2013 | Nouvel et al. | |
| 8,547,020 B2 | 10/2013 | Barroso et al. | |
| 8,552,651 B2 | 10/2013 | Sugino et al. | |
| 8,567,372 B2 | 10/2013 | Visser et al. | |
| 8,578,902 B2 | 11/2013 | Permuy et al. | |
| 8,800,539 B2 | 8/2014 | Toedter et al. | |
| 8,869,765 B2 | 10/2014 | Braeuchle | |
| 9,716,371 B2 * | 7/2017 | Burrows | H01T 19/00 |
| 2004/0129241 A1 | 7/2004 | Freen | |
| 2009/0122583 A1 | 5/2009 | Gelerter | |
| 2009/0194051 A1 | 8/2009 | Smith et al. | |
| 2009/0229581 A1 | 9/2009 | Ikeda | |
| 2010/0116257 A1 | 5/2010 | Agneray et al. | |
| 2010/0229639 A1 | 9/2010 | Agneray et al. | |
| 2010/0251995 A1 | 10/2010 | Nouvel et al. | |
| 2010/0282198 A1 | 11/2010 | Hampton et al. | |
| 2010/0313841 A1 | 12/2010 | Agneray et al. | |
| 2011/0114071 A1 | 5/2011 | Freen | |
| 2011/0146607 A1 | 6/2011 | Smith et al. | |
| 2011/0175691 A1 | 7/2011 | Smith et al. | |
| 2011/0253114 A1 | 10/2011 | Schremmer | |
| 2011/0297132 A1 | 12/2011 | Schremmer et al. | |
| 2011/0305998 A1 | 12/2011 | Toedter et al. | |
| 2012/0055430 A1 | 3/2012 | Braeuchle | |
| 2012/0055455 A1 * | 3/2012 | Ruan | F02P 23/04 |
| | | | 123/608 |
| 2012/0063054 A1 | 3/2012 | Burrows et al. | |
| 2012/0145136 A1 | 6/2012 | Burrows et al. | |
| 2012/0180742 A1 | 7/2012 | Burrows | |
| 2012/0249006 A1 | 10/2012 | Burrows | |
| 2012/0249163 A1 * | 10/2012 | Burrows | F02P 23/04 |
| | | | 324/633 |
| 2013/0208393 A1 * | 8/2013 | Hampton | F02P 9/002 |
| | | | 361/247 |
| 2013/0300474 A1 | 11/2013 | Chang et al. | |
| 2013/0308347 A1 | 11/2013 | Sato et al. | |
| 2014/0226252 A1 | 8/2014 | Freen | |
| 2015/0114331 A1 * | 4/2015 | Kernwein | H01T 19/00 |
| | | | 123/143 B |

FOREIGN PATENT DOCUMENTS

| | | |
|---|---|---|
| CN | 102562412 A | 7/2012 |
| CN | 102804527 A | 11/2012 |
| CN | 103597202 A | 2/2014 |
| DE | 19747701 A1 | 5/1999 |
| DE | 102005036968 A1 | 2/2007 |
| DE | 102010062304 A1 | 6/2012 |
| DE | 102010062305 A1 | 6/2012 |
| WO | 2010011838 A1 | 1/2010 |
| WO | 2012138674 A1 | 10/2012 |

OTHER PUBLICATIONS

International Search Report, dated Mar. 25, 2015 (PCT/US2014/069947).

International Search Report, dated Mar. 25, 2015 (PCT/US2014/069958).

International Search Report, dated Mar. 25, 2015 (PCT/US2014/069974).

* cited by examiner

RELAY-MOD METHOD TO DRIVE CORONA IGNITION SYSTEM

CROSS-REFERENCE TO RELATED APPLICATIONS

This U.S. patent application claims the benefit of U.S. provisional patent application No. 61/915,088, filed Dec. 12, 2013; U.S. provisional patent application No. 61/931,131, filed Jan. 24, 2014; U.S. provisional patent application No. 61/950,991, filed Mar. 11, 2014; U.S. provisional patent application No. 62/072,530, filed Oct. 30, 2014; and U.S. provisional patent application No. 62/090,096, filed Dec. 10, 2014, the entire contents of each being incorporated herein by reference in their entirety.

BACKGROUND OF THE INVENTION

1. Field of the Invention

This invention relates generally to a corona discharge ignition system, and more particularly to methods for controlling energy supplied to the corona igniter system.

2. Related Art

Corona discharge ignition systems provide an alternating voltage and current, reversing high and low potential electrodes in rapid succession which enhances the formation of corona discharge and minimizes the opportunity for arc formation. The system includes a corona igniter with a central electrode charged to a high radio frequency voltage potential and creating a strong radio frequency electric field in a combustion chamber. The electric field causes a portion of a mixture of fuel and air in the combustion chamber to ionize and begin dielectric breakdown, facilitating combustion of the fuel-air mixture, which is referred to as an ignition event. The electric field is preferably controlled so that the fuel-air mixture maintains dielectric properties and corona discharge occurs, also referred to as a non-thermal plasma. The ionized portion of the fuel-air mixture forms a flame front which then becomes self-sustaining and combusts the remaining portion of the fuel-air mixture. Preferably, the electric field is controlled so that the fuel-air mixture does not lose all dielectric properties, which would create a thermal plasma and an electric arc between the electrode and grounded cylinder walls, piston, metal shell, or other portion of the igniter.

In addition, preferred corona discharge ignition systems operate such that the corona igniter is driven at its resonant frequency, because resonant frequency operation allows the corona igniter to provide a high output and efficiency. However, accurately controlling the drive frequency of the corona igniter to be equal or close to the resonant frequency presents challenges; especially since the design of the corona igniter is constantly developing and improving, leading to changes in the resonant frequency. For example, one recently developed method used in effort to achieve resonant frequency operation require multiple cycles in order to achieve a lock to the correct frequency and is unable to accurately follow rapid frequency changes. Another method allows operation over only a limited range of frequencies. A third method utilizes a programmable digital or mixed-signal controller to control switches of the system with suitable timing and accuracy, but this type of controller requires complex specifications leading to high overhead and thus high costs.

SUMMARY OF THE INVENTION

One aspect of the invention provides a corona ignition system capable of operating at or near the resonant frequency of a corona igniter, and capable of quickly adjusting to changes in the resonant frequency, without a costly controller. The system includes the corona igniter receiving current at a radio frequency and providing a radio frequency electric field. A current sensor obtains an unfiltered current signal including information about the current received by the corona igniter. At least one of a signal filter and a signal conditioner receives the unfiltered current signal from the current sensor and provides a conditioned current signal, wherein the conditioned current signal includes a falling edge occurring at the end of a first time delay following a first zero crossing of the unfiltered current signal. A first timer receives the conditioned current signal and initiates a second time delay in response to the falling edge of the conditioned current signal. The first timer also provides a first timer signal, wherein the first timer signal includes a falling edge at the end of the second time delay, and the second time delay ends before a second zero crossing of the unfiltered current signal following the first zero crossing. A second timer receives the first timer signal from the first timer and provides a first output signal. A third time delay starts at the end of the second time delay at the falling edge of the first timer signal, and the first output signal includes a rising edge at the start of the third time delay. A first switch receives the first output signal and is activated at the end of the third time delay, wherein the third time delay ends at or after the second zero crossing of the unfiltered current signal. The activated first switch allows the current to flow from an energy supply to the corona igniter.

Another aspect of the invention provides a method of controlling a corona discharge system. The method includes providing energy to a corona igniter at a radio frequency; and obtaining an unfiltered current signal including information about the current received by the corona igniter. The method further includes providing a conditioned current signal which includes a falling edge occurring at the end of a first time delay following a first zero crossing of the unfiltered current signal; initiating a second time delay in response to the falling edge of the conditioned current signal and providing a first timer signal, wherein the first timer signal includes a falling edge at the end of the second time delay and the second time delay ends before a second zero crossing of the unfiltered current signal following the first zero crossing; and providing an output signal which includes a rising edge at the start of a third time delay, wherein the third time delay starts at the end of the second time delay at the falling edge of the first timer signal. The method then includes activating a first switch by the first output signal at the end of the third time delay, wherein the third time delay ends at or after the second zero crossing of the unfiltered current signal, and the activated first switch allows the current to flow from an energy supply to the corona igniter.

The system and method provides for control of the timing of the switches based on the detection of a single zero crossing of the current and hence can quickly lock on to the correct frequency and quickly respond to changes in the resonant frequency. The timers used to activate the switches can be programmed over a wide range of intervals allowing a wide range of drive frequencies to be accommodated. In addition, the generation of timing signals by the timers to activate the switches is independent from the other functions of the controller, for example, communication with the vehicle, management of power supplies and so on. This separation allows the computational load on the controller to be greatly reduced, and thus allows the use of fewer and/or cheaper controllers. Accordingly, the present invention provides a more cost effective system and method for maintaining the drive frequency at or close to the resonant frequency of the corona igniter, while still allowing for high resolution control.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
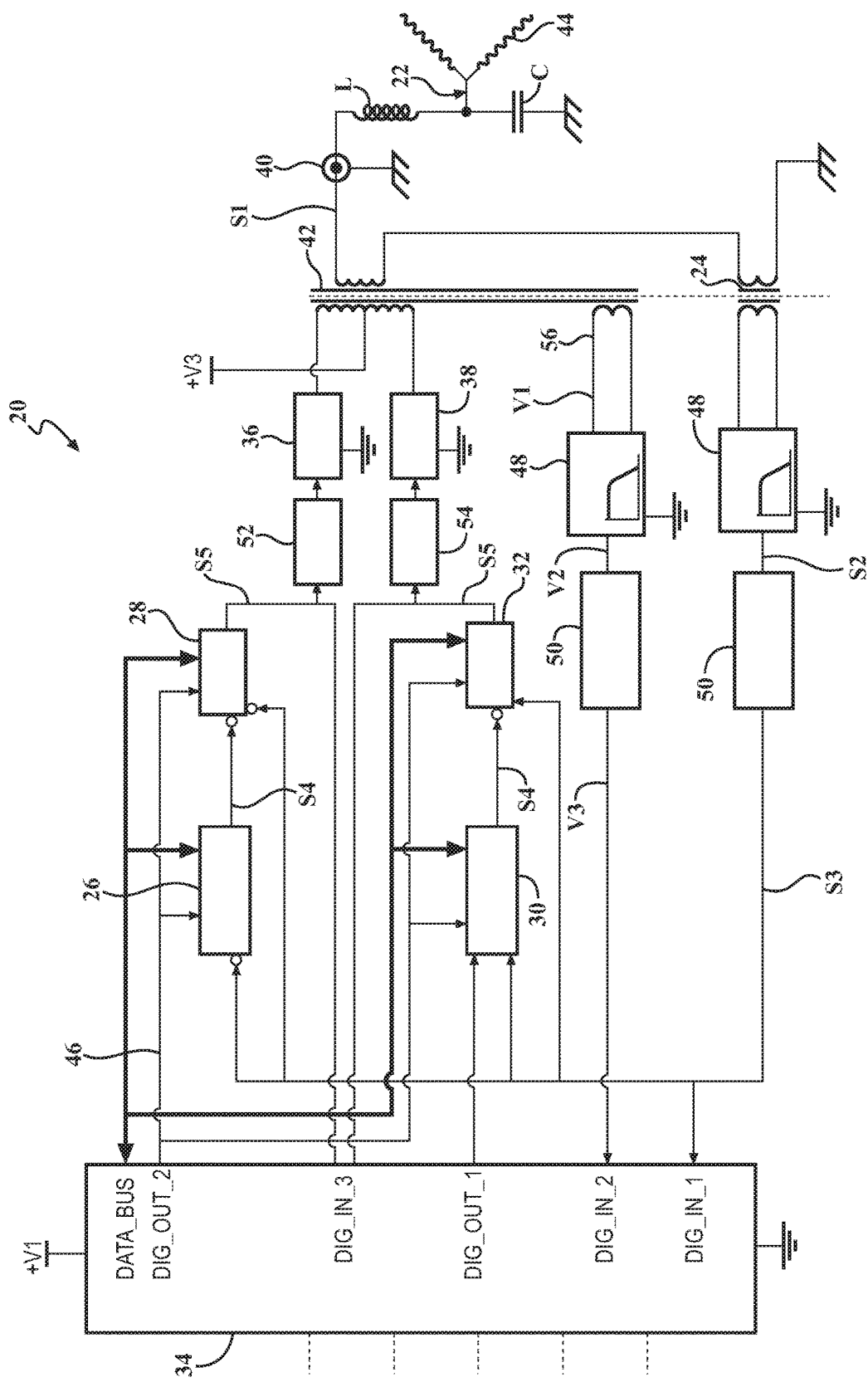
FIG. 1 is a block diagram of a corona discharge ignition system according to a first exemplary embodiment of the invention.

One aspect of the invention provides a cost effective corona ignition system 20 for accurately maintaining a drive frequency approximately equal to the resonant frequency of a corona igniter 22 of the system 20. In addition to the corona igniter 22, the system 20 also includes a current sensor 24, at least two cascaded timers 26, 28, 30, 32 which are electrically independent of a controller 34, and at least two switches 36, 38. During operation, the current sensor 24 measures the current at an input 40 of the corona igniter 22. A conditioned current signal S3 including information related to the current ultimately activates a pair of the timers 26, 28, 30, 32 which in turn control and drive one of the switches 36, 38. Unlike the comparative systems 20, the conditioned current signal S3 is not processed by the controller 34 before driving the switch 36 or 38.

The system 20 and method provides for control of the timing of the switches 36, 38 based on the detection of a single zero crossing of the current and hence can quickly lock on to the correct frequency and quickly respond to changes in the resonant frequency. The timers 26, 28, 30, 32 used to activate the switches 36, 38 can be programmed over a wide range of intervals allowing a wide range of drive frequencies to be accommodated. In addition, the generation of output signals S5 from the timers 26, 28, 30, 32 to activate the switches 36, 38 is independent from the other functions of the controller 34, for example, communication with the vehicle, management of power supplies and so on. This separation allows the computational load on the controller 34 to be greatly reduced, and thus allows the use of fewer and/or cheaper controllers 34. Accordingly, a more cost effective system 20 and method for maintaining the drive frequency at or close to the resonant frequency of the corona igniter 22, while still allowing for high resolution control, is achieved.

FIG. 1 illustrates a corona ignition system 20 according to an exemplary embodiment of the invention which accommodates a wide range of drive frequencies, for example 700 kHz to 2 MHz, but requires a less costly controller 34, without compromising the performance of the system 20. The system 20 of FIG. 1 includes an energy supply +V3 for providing energy to a transformer 42 and then to the corona igniter 22. To begin a corona discharge 44 process, the controller 34 initiates an enable signal 46 to one of the timers 26, 28, 30, 32 to activate the first switch 36 and allow current to flow from the energy supply +V3 through the transformer 42 and to the corona igniter 22.

The corona igniter 22 receives current at a radio frequency and provides a radio frequency electric field, referred to as corona discharge 44. The current sensor 24 obtains information about the current provided to the corona igniter 22 at an output of the transformer 42, also referred to as an input 40 of the corona igniter 22. The current sensor 24 obtains this information in the form of an unfiltered current signal S1 which includes high frequency noise.

Figure 2:
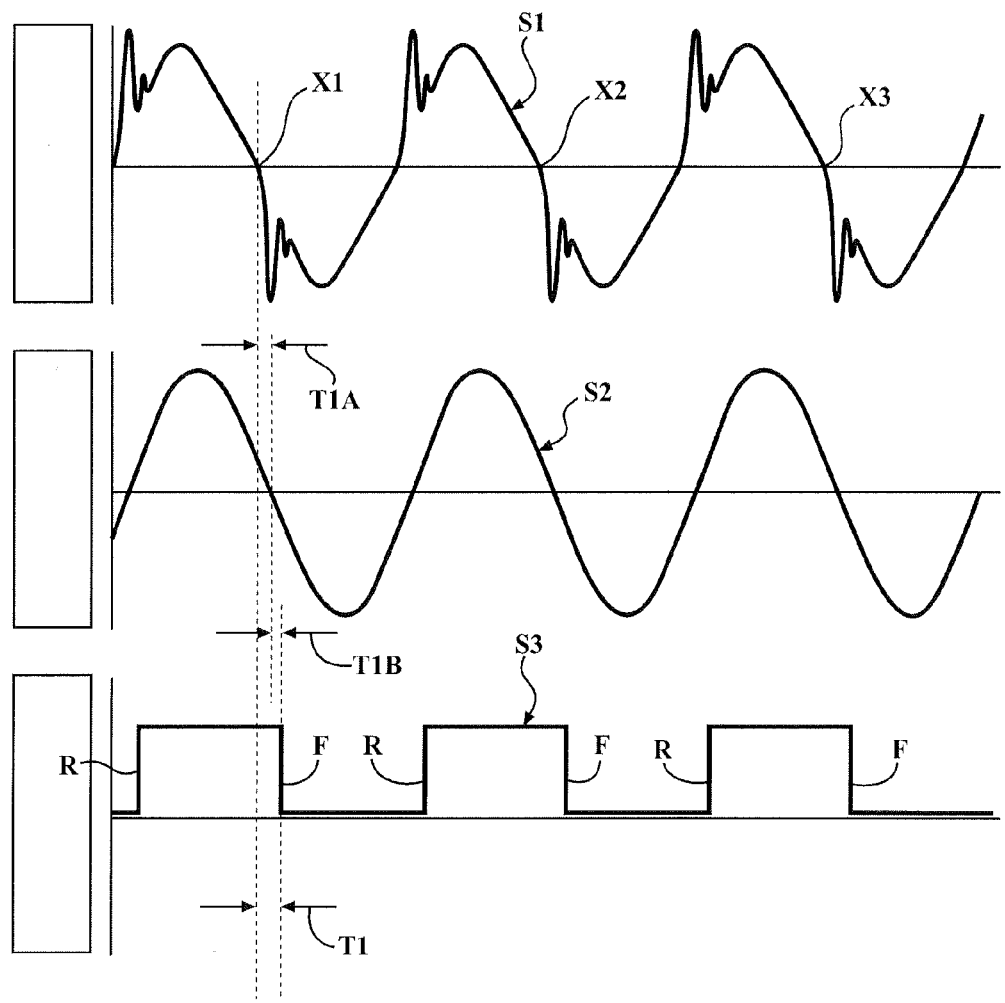
FIG. 2 includes graphs of an unfiltered current signal S1 illustrating current at an input of a corona igniter of the system of FIG. 1, a filtered current signal S2 closely resembling the current at the corona igniter, and a conditioned current signal S3 indicating the phase of the current at the corona igniter, according to an exemplary embodiment.

Before conveying the current information toward a pair of the cascaded timers 26, 28, 30, 32, the current sensor 24 conveys the unfiltered current signal S1 to at least one of a signal filter 48, such as a low-pass filter, and a signal conditioner 50. The signal filter 48 can remove high frequency noise from the signal, if required. The signal conditioner 50 can extract information about the phase of the current. At this point, a conditioned current signal S3 is provided, which typically contains only information relating to the phase (direction of current flow) at the input 40 offset by a time delay due to the current sensor 24, signal filter 48, and signal conditioner 50. FIG. 2 includes graphs showing current signals S1, S2, S3 which include information about the current at the input 40 to the corona igniter 22. In one embodiment, the conditioned current signal S3 includes a falling edge F occurring at the end of a first time delay T1 following a first zero crossing X1 of the unfiltered current signal S1. The first time delay T1 is caused by a time delay T1A of the current sensor 24 and a time delay T1B of the signal filter 48. Both T1A and T1B are known and can be compensated for by the controller 34. The time delays T1A and T1B added together equal the first time delay T1. The first time delay T1 is deterministic and may be known and therefore compensated by the controller 34.

Unlike comparative systems 20, the conditioned current signal S3 is not sent to the controller 34 to be processed and to produce signals that drive the switches 36, 38. Rather, the current information is used to directly trigger a pair of the cascaded timers 26, 28, 30, 32 which in turn control the timing of one of the switches 36, 38 through a driver 52 or 54. The cascaded timers 26, 28, 30, 32 are electrically independent of the controller 34, and thus the resolution of the timers 26, 28, 30, 32 is independent of the clock speed of the processing unit of the controller 34.

Figure 3:
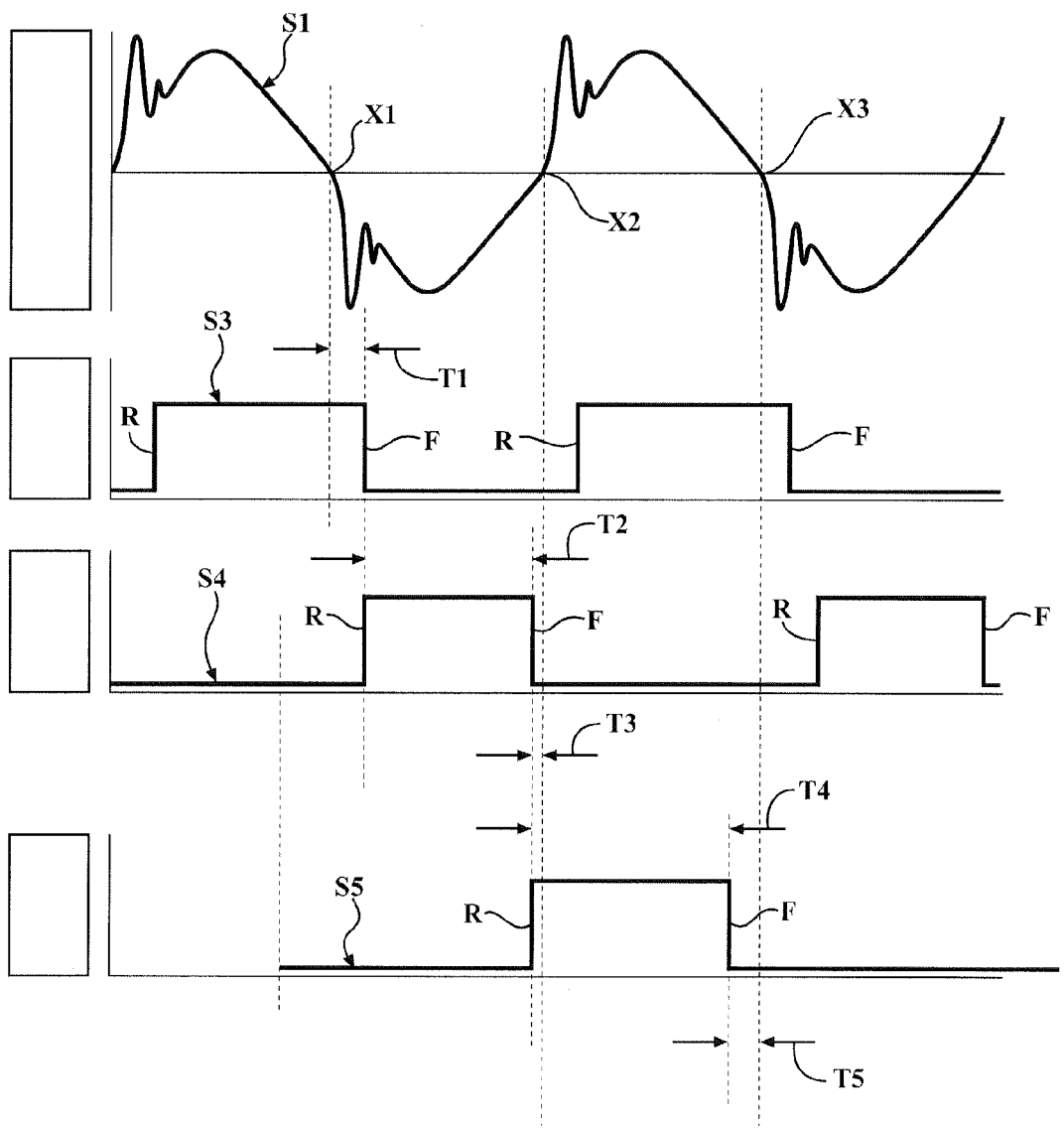
FIG. 3 includes graphs illustrating how the conditioned current signal S3 of FIG. 2 is used to control energy provided to the corona igniter according to an exemplary embodiment.

In the exemplary embodiment of FIGS. 1-3, a first timer 26 receives the conditioned current signal S3 and initiates a second time delay T2 in response to the falling edge F of the conditioned current signal S3. The first timer 26 also provides a first timer signal S4, wherein the first timer signal S4 includes a falling edge F at the end of the second time delay T2. The second time delay T2 ends before a second zero crossing X2 of the unfiltered current signal S1 following the first zero crossing X1. A second timer 28 receives the first timer signal S4 from the first timer 26 and provides a first output signal S5. A third time delay T3 starts at the end of the second time delay T2 at the falling edge F of the first timer signal S4, and the first output signal S5 includes a rising edge R at the start of the third time delay T3. The first switch 36 receives the first output signal S5 and is activated at the end of the third time delay T3. In this exemplary embodiment, the third time delay T3 ends at or after the second zero crossing X2 of the unfiltered current signal S1. The activated first switch 36 allows the current to flow from an energy supply +V3 to the corona igniter 22.

In the exemplary embodiment of FIGS. 1-3, the second timer 28 also initiates a fourth time delay T4 starting at the rising edge R of the first output signal S5 and ending at a falling edge F of the first output signal S5. The end of the fourth time delay T4 occurs before a third zero crossing X3 of the unfiltered current signal S1. The first switch 36 is deactivated at the end of a fifth time delay T5 which starts at the falling edge F of the first output signal S5 and ends before or at the third zero crossing X3.

In the system 20 of claim 1, the controller 34 sets the second time delay T2 and the fourth time delay T4 so that the first switch 36 activated or deactivated at or adjacent one of the zero crossings X1, X2, X3 of the current received by the corona igniter 22. The conditioned current signal S3 is sampled by the controller 34 via the digital input (DIG IN) and compared to the voltage to determine whether adjustments to the second time delay T2 or the fourth time delay T4 should be made. A voltage sensor 56 can be used to measure the voltage at the input 40 to the corona igniter 22 and then provide an unfiltered voltage signal V1, which is filtered to provide a filtered voltage signal V2, conditioned to provide a conditioned voltage signal V3, and conveyed in the conditioned voltage signal V3 to the controller 34. The controller 34 then compares the conditioned voltage signal V3 to the conditioned current signal S3, adjusts at least one of the second time delay T2 and the fourth time delay T4 if zero crossings X1, X2, X3 of the unfiltered current signal S1 are not simultaneous with the zero crossings of the unfiltered voltage signal V1 at the input 40. However, the controller 34 only needs to check for errors and make adjustments from time to time, not every cycle. Typically, the conditioned current signal S3 is conveyed from the current sensor 24 to the first switch 36 without being conveyed to the controller 34 prior to being conveyed to the first switch 36.

Once the controller 34 initiates the enable signal 46, the process described above, including the signals S1, S2, S3, S4, S5 and time delays T1, T2, T3, T4, T5, repeats continuously. The process proceeds to use the third timer 30, the fourth timer 32, the second driver 54, and the second switch 38. For example, in the exemplary embodiment, a sixth time delay follows the fifth time delay T5, and the conditioned current signal S3 includes a rising edge occurring at the end of the sixth time delay following a fourth zero crossing of the unfiltered current signal S1. The duration of the sixth time delay is equal to the duration of the first time delay T1. A third timer 30 receives the conditioned current signal S3 and initiates a seventh time delay in response to a rising edge of the conditioned current signal S3 and provides a second timer signal S4. The seventh time delay is equal to the second time delay T2, the second timer signal S4 includes a rising edge at the end of the seventh time delay, and the seventh time delay ends before a fifth zero crossing of the unfiltered current signal S1 following the fourth zero crossing. The fourth timer 32 receives the timer signal S4 from the third timer 30 and provides a second output signal S5. An eighth time delay starts at the end of the seventh time delay at the rising edge of the timer signal S4. The eighth time delay is equal to the third time delay T3, and the second output signal S5 includes a falling edge F at the start of the eighth time delay. The second switch 38 receives the second output signal S5 and is activated at the end of the eighth time delay, wherein the eighth time delay ends at or after the fifth zero crossing of the unfiltered current signal S1, and the activated second switch 38 allows the current to flow from the energy supply +V3 to the corona igniter 22.

In this exemplary embodiment, the fourth timer 32 initiates a ninth time delay starting at the falling edge F of the second output signal S5 and ending at a rising edge of the second output signal S5. The ninth time delay is equal to the fourth time delay T4, and the end of the ninth time delay occurs before a sixth zero crossing of the unfiltered current signal S1. The second switch 38 is deactivated at the end of a tenth time delay which starts at the rising edge R of the second output signal S5 and ends before or at the sixth zero crossing. The tenth time delay is equal to the fifth time delay T5.

The controller 34 sets the seventh time delay and the ninth time delay so that the switch is activated or deactivated at or adjacent one of the zero crossings of the unfiltered current signal S1, just like the third time delay T3 and the fifth time delay T5. The first, third, fifth, sixth, eighth, and tenth time delays are fixed and based at least in part on design of the current sensor 24, the signal filter 48 and/or the signal conditioner 50, the timers 26, 28, 30, 32 and the switches 36, 38. The controller 34 however adjusts at least one of the second time delay T2 and the fourth time delay T4 if zero crossings of the voltage received by the corona igniter 22 are not simultaneous with the zero crossings of the unfiltered current signal S1 which represents the current received by the corona igniter 22.

It is noted that the voltage sampling may be omitted if the controller 34 is adequately able to compensate for delays T1, T2, T3, T4, T5 in all elements of the current control loop, including the current sensor 24, signal filter 48, signal conditioner 50, timers 26, 28, 30, 32, switches 36, 38, drivers 52, 54, and the transformer 42. In addition, one or more of the elements in the loop may be omitted or modified depending on the requirements of the specific installation. For example, the timers 26, 28, 30, 32 may be able to operate the switches 36, 38 without the use of the separate drivers 52, 54. In another example, the timers 26, 28, 30, 32 are physically located in the controller 34, while still being electrically independent from the processing unit. In another example, the current sensor 24 has suitable frequency response characteristics and thus the signal filter 48 is not required.

Monitoring the relative timing of the conditioned current signal S3 and the conditioned voltage signal V3, or the voltage at the input 40, allows the drive frequency of the system 20 to be maintained accurately at or close to the resonant frequency of current at the input 40 to the corona igniter 22, but without requiring the controller 34 to accurately generate all of the control signals. The timers 26, 28, 30, 32 may be driven using a clock of different, and typically higher, speed than the controller 34 in order to achieve the required accuracy without requiring a faster and hence more expensive controller 34. In addition, a dead-time may be included when using the switches 52, 54 in this configuration. The dead-time is a brief period of time that occurs while changing from one switch 52, 54 to another to allow conduction in one switch 52, 54 to completely cut off before enabling conduction in another to avoid overlap of current flow through both switches 52, 54 at the same time. This dead-time may easily be implemented in this scheme by adjustment of the timer intervals T4 and T6.

Figure 4:
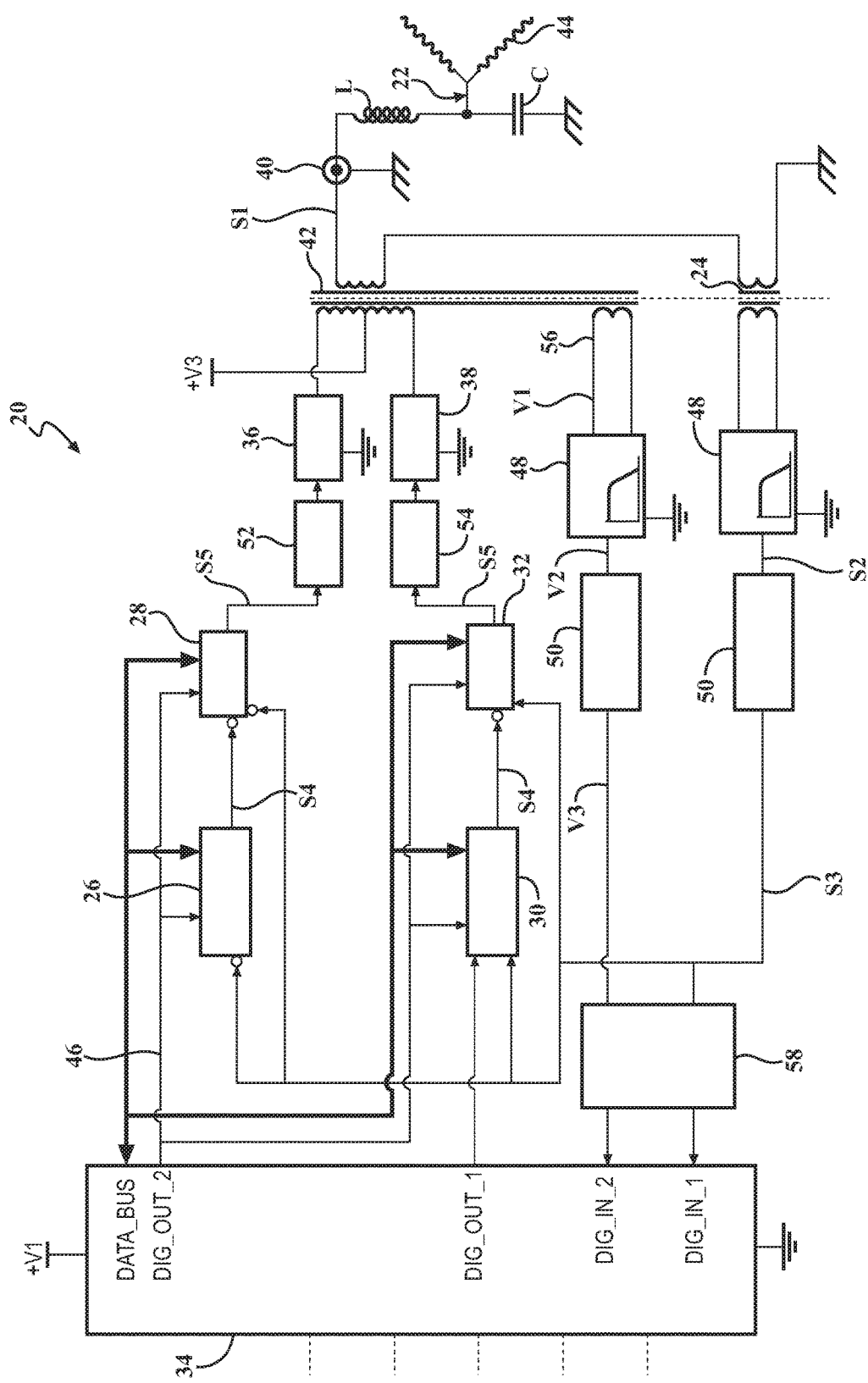
FIG. 4 is a block diagram of a corona discharge ignition system according to a second exemplary embodiment of the invention.

FIG. 4 shows a corona discharge 44 ignition system 20 according to another exemplary embodiment of the invention. In this embodiment, a separate phase detector 58 compares the phase difference between the conditioned current signal S3 and the conditioned voltage signal to identify errors, for example if the current passes through zero before or after the voltage passes through zero, in which case the system 20 is not at resonance. The phase detector 58 provides the identified error and a direction signal which is passed to the controller 34 via the digital inputs. The controller 34 can then adjust the fourth time delay T4 and the sixth time delay T6 accordingly to correct the error, for example speed up or slow down the process, so that the current and voltage cross through zero simultaneously. The design of the phase detector 58 can be selected from those well known in the art, as phase detectors 58 are commonly used in circuits to control a phase-locked loop (PLL), for example. This phase detector 58 may compare the phase of the conditioned current signal S3 with the phase of the conditioned voltage signal. Alternatively, the phase detector 58 can compare the phase of the conditioned current signal S3 with the voltage phase derived from any other point in the loop as previously described, for example, at the timer signal or output signal S5. It is noted that other methods of resonant frequency control which can be employed in the system described herein are disclosed in related U.S. patent application Ser. Nos. 14/568,219, 14/568,266, and 14/568,438, which are incorporated herein by reference. In addition, each of those applications discloses systems with components that can be incorporated into the present system 20. Each application lists the same inventor and was filed on the same day as the present application.

As indicated above, the system 20 of the present invention includes cascaded timers 26, 28, 30, 32 which are electrically independent from the controller 34 of the system 20 and can be triggered directly by hardware signals derived from measurements of the behavior of the current and voltage in the corona igniter 22. These timers 26, 28, 30, 32 then directly activate switches 36, 38 controlling the circuit which drives the frequency of the power fed to the corona igniter 22. The controller 34 only needs to supervise the timers 26, 28, 30, 32 to ensure they are properly configured, instead of having to monitor feedback signals and correctly activate the switches 36, 38 directly. The resolution of the timers 26, 28, 30, 32 is therefore independent of the clock speed of the processing unit of the controller 34.

The cascaded timers 26, 28, 30, 32 also allow for a slower, cheaper processing unit to be used in the controller 34 without compromising system performance. Thus, the processing overhead is greatly reduced. Although a programmable digital or mixed-signal controller 34 to ensure accurate frequency control offers several advantages, the high accuracy required in frequency control leads to a high resolution requirement in the controller 34, often leading to a high computational load on the processing unit, and requiring a high clock speed and hence higher costs. In addition, the timers 26, 28, 30, 32 can be programmed over a wide range of intervals which allows a wide range of drive frequencies to be used.

Obviously, many modifications and variations of the present invention are possible in light of the above teachings and may be practiced otherwise than as specifically described while within the scope of the claims.

What is claimed is:

1. A corona ignition system, comprising:
a corona igniter receiving current at a radio frequency and providing a radio frequency electric field;
a current sensor obtaining an unfiltered current signal including information about the current received by the corona igniter;
at least one of a signal filter and a signal conditioner receiving the unfiltered current signal from the current sensor and providing a conditioned current signal, wherein the conditioned current signal includes a falling edge occurring at the end of a first time delay following a first zero crossing of the unfiltered current signal;
a first timer receiving the conditioned current signal and initiating a second time delay in response to the falling edge of the conditioned current signal and providing a first timer signal, wherein the first timer signal includes a falling edge at the end of the second time delay and the second time delay ends before a second zero crossing of the unfiltered current signal following the first zero crossing;
a second timer receiving the first timer signal from the first timer and providing a first output signal, wherein a third time delay starts at the end of the second time delay at the falling edge of the first timer signal, and the first output signal includes a rising edge at the start of the third time delay; and
a first switch receiving the first output signal and being activated at the end of the third time delay, wherein the third time delay ends at or after the second zero crossing of the unfiltered current signal, and the activated first switch allows the current to flow from an energy supply to the corona igniter.

2. The system of claim 1, wherein the second timer initiates a fourth time delay starting at the rising edge of the first output signal and ending at a falling edge of the first output signal, the end of the fourth time delay occurs before a third zero crossing of the unfiltered current signal, the first switch is deactivated at the end of a fifth time delay which starts at the falling edge of the first output signal and ends before or at the third zero crossing.

3. The system of claim 2 including a controller setting the second time delay and the fourth time delay so that the first switch is activated or deactivated at or adjacent one of the zero crossings of the current received by the corona igniter.

4. The system of claim 3, wherein the controller receives a voltage, and the controller adjusts at least one of the second time delay and the fourth time delay if zero crossings of the unfiltered current signal are not simultaneous with the zero crossings of the unfiltered current signal.

5. The system of claim 3, wherein the controller initiates an enable signal to one of the timers to activate the first switch and allow the current to flow from the energy supply to the corona igniter before the current sensor obtains the information about the current.

6. The system of claim 3, wherein the timers are electrically independent of the controller.

7. The system of claim 1, wherein the conditioned current signal is conveyed from the signal conditioner to the first timer without the controller acting as an intermediary.

8. The system of claim 1, wherein the conditioned current signal includes a rising edge occurring at the end of a sixth time delay following a fourth zero crossing of the unfiltered current signal, wherein the sixth time delay is equal to the first time delay;
a third timer receives the conditioned current signal and initiates a seventh time delay in response to a rising edge of the conditioned current signal and provides a second timer signal, wherein the seventh time delay is equal to the second time delay, the second timer signal includes a rising edge at the end of the seventh time delay and the seventh time delay ends before a fifth zero crossing of the unfiltered current signal following the fourth zero crossing; a fourth timer receives the first timer signal from the third timer and provides a second output signal, wherein an eighth time delay starts at the end of the seventh time delay at the rising edge of the first timer signal, the eighth time delay is equal to the third time delay, and the second output signal includes a falling edge at the start of the eighth time delay; and a second switch receives the second output signal and is activated at the end of the eighth time delay, wherein the eighth time delay ends at or after the fifth zero crossing of the unfiltered current signal, and the activated second switch allows the current to flow from the energy supply to the corona igniter.

9. The system of claim 8, wherein the fourth timer initiates a ninth time delay starting at the falling edge of the second output signal and ending at a rising edge of the second output signal, the ninth time delay is equal to the fourth time delay, the end of the ninth time delay occurs before a sixth zero crossing of the unfiltered current signal, the second switch is deactivated at the end of a tenth time delay which starts at the rising edge of the second output signal and ends before or at the sixth zero crossing, and the tenth time delay is equal to the fifth time delay.

10. The system of claim 9 including a controller setting the seventh time delay and the ninth time delay so that the switch is activated or deactivated at or adjacent one of the zero crossings of the unfiltered current signal.

11. The system of claim 10, wherein the corona igniter receives a voltage and the controller adjusts at least one of the second time delay and the fourth time delay if zero crossings of the voltage received by the corona igniter are not simultaneous with the zero crossings of the unfiltered current signal.

12. The system of claim 10, wherein the first, third, fifth, sixth, eighth, and tenth time delays are fixed and based at least in part on design of the current sensor, the signal filter and/or the signal conditioner, the timers, and the switches.

13. A method of controlling a corona discharge system, comprising the steps of:

providing energy to a corona igniter at a radio frequency;

obtaining an unfiltered current signal including information about the current received by the corona igniter;

providing a conditioned current signal which includes a falling edge occurring at the end of a first time delay following a first zero crossing of the unfiltered current signal;

initiating a second time delay in response to the falling edge of the conditioned current signal and providing a first timer signal, wherein the first timer signal includes a falling edge at the end of the second time delay and the second time delay ends before a second zero crossing of the unfiltered current signal following the first zero crossing;

providing an output signal which includes a rising edge at the start of a third time delay, wherein the third time delay starts at the end of the second time delay at the falling edge of the first timer signal; and activating a first switch by the first output signal at the end of the third time delay, wherein the third time delay ends at or after the second zero crossing of the unfiltered current signal, and the activated first switch allows the current to flow from an energy supply to the corona igniter.

14. The method of claim 13 including initiating a fourth time delay starting at the rising edge of the first output signal and ending at a falling edge of the first output signal, the end of the fourth time delay occurs before a third zero crossing of the unfiltered current signal, and deactivating the first switch at the end of a fifth time delay which starts at the falling edge of the first output signal and ends before or at the third zero crossing.

15. The method of claim 13 including setting the second time delay and the fourth time delay so that the first switch is activated or deactivated at or adjacent one of the zero crossings of the current received by the corona igniter.

16. The method of claim 13 including adjusting at least one of the second time delay and the fourth time delay if zero crossings of the unfiltered current signal are not simultaneous with the zero crossings of the unfiltered current signal.

17. The method of claim 13 including initiating an enable signal to one of the timers to activate the first switch and allow the current to flow from the energy supply to the corona igniter before the current sensor obtains the information about the current.

18. The method of claim 13, wherein the conditioned current signal is conveyed from the signal conditioner to the first timer without a controller acting as an intermediary.

19. The method of claim 13, wherein the conditioned current signal includes a rising edge occurring at the end of a sixth time delay following a fourth zero crossing of the unfiltered current signal, wherein the sixth time delay is equal to the first time delay;

initiating a seventh time delay in response to a rising edge of the conditioned current signal and providing a second timer signal, wherein the seventh time delay is equal to the second time delay, the second timer signal includes a rising edge at the end of the seventh time delay and the seventh time delay ends before a fifth zero crossing of the unfiltered current signal following the fourth zero crossing;

providing a second output signal including a falling edge at the start of an eighth time delay, wherein the eighth time delay starts at the end of the seventh time delay at the rising edge of the second timer signal, the eighth time delay is equal to the third time delay;

activating a second switch by the second output signal at the end of the eighth time delay, wherein the eighth time delay ends at or after the fifth zero crossing of the unfiltered current signal, and the activated second switch allows the current to flow from the energy supply to the corona igniter;

initiating a ninth time delay starting at the falling edge of the second output signal and ending at a rising edge of the second output signal, wherein the ninth time delay is equal to the fourth time delay, and the end of the ninth time delay occurs before a sixth zero crossing of the unfiltered current signal; and deactivating the second switch at the end of a tenth time delay which starts at the rising edge of the second output signal and ends before or at the sixth zero crossing, wherein the tenth time delay is equal to the fifth time delay.

20. The method of claim 19, including adjusting at least one of the eighth and tenth time delays if zero crossings of the voltage received by the corona igniter are not simultaneous with the zero crossings of the unfiltered current signal.

* * * * *